US011571589B2

(12) United States Patent
Geraats et al.

(10) Patent No.: US 11,571,589 B2
(45) Date of Patent: Feb. 7, 2023

(54) SYSTEM FOR ASSISTING IN PERFORMING AN INTERVENTIONAL PROCEDURE

(71) Applicant: KONINKLIJKE PHILIPS N.V., Eindhoven (NL)

(72) Inventors: Jacobus Sigbertus Marie Geraats, Eindhoven (NL); Guillaume Leopold Theodorus Frederik Hautvast, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 307 days.

(21) Appl. No.: 16/078,308

(22) PCT Filed: Mar. 15, 2017

(86) PCT No.: PCT/EP2017/056051
§ 371 (c)(1),
(2) Date: Aug. 21, 2018

(87) PCT Pub. No.: WO2017/157974
PCT Pub. Date: Sep. 21, 2017

(65) Prior Publication Data
US 2019/0060666 A1    Feb. 28, 2019

(30) Foreign Application Priority Data

Mar. 16, 2016  (EP) .................... 16160635

(51) Int. Cl.
*A61N 5/10* (2006.01)
*A61B 34/20* (2016.01)
(Continued)

(52) U.S. Cl.
CPC ............ *A61N 5/1027* (2013.01); *A61B 34/20* (2016.02); *A61B 90/37* (2016.02); *A61N 5/1039* (2013.01);
(Continued)

(58) Field of Classification Search
CPC .. A61N 5/1001; A61N 5/1002; A61N 5/1007; A61N 5/1027; A61N 5/103; A61N 5/1049
See application file for complete search history.

(56) References Cited

U.S. PATENT DOCUMENTS

| 4,048,454 | A | 9/1977 | Barcus et al. |
| 9,101,395 | B2 | 8/2015 | Gutierrez et al. |
| 2002/0038117 | A1* | 3/2002 | Tokita .................. A61N 5/1007 606/1 |
| 2003/0065260 | A1 | 4/2003 | Cheng et al. |

(Continued)

FOREIGN PATENT DOCUMENTS

| WO | 2015011690 A2 | 1/2015 |
| WO | 2015044071 A1 | 4/2015 |

OTHER PUBLICATIONS

"A Practical Guide to Quality Control of Brachytherapy Equipment" edited by J. Venselaar and J. Perez-Catatayud, European Society for Therapeutic Radiology and Oncology (2004).

*Primary Examiner* — Carrie R Dorna
(74) *Attorney, Agent, or Firm* — Sherry Austin

(57) ABSTRACT

A system for assisting in performing an interventional procedure includes a first subsystem (1) and a second subsystem at different places, especially in different rooms. At a first place the first subsystem a) generates a first image of a subject (22) while an interventional device (12) is introduced into the subject and b) determines the position of the interventional device within the subject. At a second place the second subsystem a) generates a second image of the subject with the introduced interventional device and b) plans and/or monitors a treatment based on the second image and the already determined position of the interventional device, i.e. the second subsystem does not need to start a completely new position determination procedure, thereby reducing technical efforts. Moreover, the first and second images are generated by different imaging modalities which allows for, for instance, improved image guidance, planning and/or monitoring.

19 Claims, 7 Drawing Sheets

(51) Int. Cl.
*A61B 90/00* (2016.01)
*A61B 17/00* (2006.01)
*A61B 18/00* (2006.01)

(52) U.S. Cl.
CPC ......... *A61N 5/1049* (2013.01); *A61N 5/1065* (2013.01); *A61B 2017/00274* (2013.01); *A61B 2018/00547* (2013.01); *A61B 2034/2051* (2016.02); *A61B 2034/2055* (2016.02); *A61B 2034/2063* (2016.02); *A61B 2090/364* (2016.02); *A61B 2090/374* (2016.02); *A61B 2090/3762* (2016.02); *A61B 2090/3784* (2016.02); *A61B 2090/397* (2016.02); *A61N 2005/1051* (2013.01); *A61N 2005/1052* (2013.01); *A61N 2005/1055* (2013.01); *A61N 2005/1058* (2013.01); *A61N 2005/1061* (2013.01)

(56) References Cited

U.S. PATENT DOCUMENTS

| | | |
|---|---|---|
| 2004/0225174 A1* | 11/2004 | Fuller ................. G16H 30/20 600/1 |
| 2007/0078327 A1 | 4/2007 | Kindlein |
| 2007/0265521 A1 | 11/2007 | Redel et al. |
| 2011/0166410 A1* | 7/2011 | Gutierrez ............. A61N 5/1015 600/8 |
| 2012/0035462 A1 | 2/2012 | Maurer et al. |
| 2012/0071749 A1 | 3/2012 | Xu et al. |
| 2014/0275962 A1 | 9/2014 | Foo et al. |
| 2015/0190653 A1 | 7/2015 | Bharat et al. |
| 2015/0313571 A1 | 11/2015 | Yang et al. |
| 2016/0000519 A1 | 1/2016 | Dehghan |
| 2016/0120524 A1 | 5/2016 | Suehira |
| 2016/0310219 A1 | 10/2016 | Weiss |
| 2017/0120072 A1* | 5/2017 | Van De Wardt ....... A61B 34/20 |

* cited by examiner

SYSTEM FOR ASSISTING IN PERFORMING AN INTERVENTIONAL PROCEDURE

CROSS-REFERENCE TO PRIOR APPLICATIONS

This application is the U.S. National Phase application under 35 U.S.C. § 371 of International Application Serial No. PCT/EP2017/056051, filed on Mar. 15, 2017, which claims the benefit of European Patent Application No. 16160635.5, filed on Mar. 16, 2016. This application is hereby incorporated by reference herein.

FIELD OF THE INVENTION

The invention relates to a system, method and computer program for assisting in performing an interventional procedure like a brachytherapy procedure.

BACKGROUND OF THE INVENTION

US 2011/0166410 A1 (Gutierrez) discloses a brachytherapy system for a target region comprising an applicator having a plurality of channels that are hollow and expandable, wherein the applicator is adapted to be implanted in the target region. The system further comprises a tracking device, a tracking signal generator to generate a signal received by the tracking device and a processor. The tracking device has a size and shape to be advanced and retracted through at least a portion of the plurality of channels. The processor determines a position of one or more of the plurality of channels based on a movement of the tracking device, wherein the processor determines a location of one or more of the plurality of channels in an image based at least in part on a position measurement from the tracking device.

US 2007/0078327 A1 (Kindlein) discloses a system for effecting radiation treatment on a pre-selected anatomical portion of an animal body, wherein the system comprises a first imaging means for generating image information of the pre-selected anatomical portion to be treated and processing means for generating a radiation treatment plan partly based on the image information for effecting the radiation therapy on the pre-selected anatomical portion, wherein the treatment plan includes information concerning a number, position and direction of a plurality of hollow treatment channels to be inserted within the anatomical portion, one or more positions and corresponding times of one or more radiation emitting sources to be inserted through the plurality of hollow treatment channels, and the amount of radiation dose to be emitted. The system further comprises insertion means for inserting the plurality of hollow treatment channels at the planned positions and directions into the anatomical portion and radiation delivery means for inserting at least one energy emitting source through the plurality of hollow treatment channels at the one or more positions into the anatomical portion. Identifying means are present for identifying the location of at least one treatment channel from the group of the plurality of inserted treatment channels, wherein the identified location is compared with one or more of the pre-planned locations present in the treatment plan.

US 2003/0065260 A1 (Cheng) discloses a system for identifying and quantifying departures in the placement of needles or catheters from intended placements in a treatment plan for treating an organ. The needles or catheters carry therapeutic agents for insertion into the organ for use in the treatment plan. The system comprises an imaging device for imaging the organ, an intraoperative tracking interface comprising a display, and a computing device in electronic communication with the intraoperative tracking interface. The computing device is adapted to input the intended placements into the intraoperative tracking interface and to, for at least one needle or catheter, calculate a difference in an x-y plane between the intended placement of that needle or catheter and an actual placement of that needle or catheter. Moreover, the computing device is adapted to calculate, from the calculated difference in the x-y plane, a position error for each of the therapeutic agents, to adjust positions of therapeutic agents along each needle or catheter by an amount to be determined in accordance with the calculated position error and to determine positions of a deposited number of therapeutic agents through imaging carried out by the imaging device.

An interventional system is, for instance, a high-dose rate (HDR) brachytherapy system which comprises several brachytherapy catheters to be introduced into a target region. Within the brachytherapy catheters a radioactive radiation source is moved to different dwell positions at which the radioactive radiation source is located for respective dwell times, in order to treat the target region by radioactive radiation emitted by the radioactive radiation source.

The brachytherapy catheters are introduced into the target region while a real-time ultrasound image of the target region is generated and shown to the physician. Moreover, the real-time ultrasound image can be overlaid with a pre-interventional image of the target region, which has been generated by, for instance, a magnetic resonance (MR) imaging device or a computed tomography (CT) imaging device. These images guide the physician while introducing the brachytherapy catheters into the target region. However, even by using this image-based guidance of the physician, the brachytherapy catheters may not be placed accurately enough, which may lead to a reduced quality of the outcome of the brachytherapy procedure.

SUMMARY OF THE INVENTION

It is an object of the present invention to provide a system, method and computer program for assisting in performing an interventional procedure, which allow for an improved outcome of the interventional procedure.

In a first aspect of the present invention a system for assisting in performing an interventional procedure is presented, wherein the system comprises:
  a first subsystem comprising a) a first imaging device for generating a first image of a subject while an interventional device is introduced into the subject, b) a position determination device for determining the position of the interventional device within the subject relative to the first image, and c) a storage for storing the determined position of the interventional device within the subject, after the interventional device has been introduced into the subject,
  a second subsystem comprising a) a second imaging device for generating a second image of the subject with the introduced interventional device, wherein the first and second imaging devices are different imaging modalities, and b) a planning and/or monitoring device for planning a treatment to be performed by using the interventional device and/or for monitoring a treatment performed by using the interventional device based on the stored position of the interventional device and the second image, wherein the first subsystem and the second subsystem are located at different places.

Since the first and second images, which have been generated at different places, i.e., for instance, in different rooms, have been generated by different imaging modalities, they may show same features differently and/or a feature not visible in one of these images may be visible in the other of these images. This can lead to an improved image guidance, treatment planning and/or treatment monitoring and hence to an improved outcome of the interventional procedure. For instance, the first interventional image may be an interventional ultrasound image, which can be used for guiding a physician while introducing a brachytherapy catheter into a subject, wherein the second interventional image can be an MR image in which a target region is well recognizable and which can be used for accurately placing a radioactive radiation source within the brachytherapy catheter such that the target region is treated by the radiation emitted by the radiation source.

Moreover, since the position of the interventional device, which has been determined by the position determination device of the first subsystem, is provided to the second subsystem, the position of the interventional device can be used together with the second image for treatment planning and/or treatment monitoring, without requiring the second subsystem to start a completely new position determination procedure for determining the position of the interventional device. For instance, the second subsystem can just use the position determined by the first subsystem or determine the position of the interventional device by identifying the interventional device in the second image under consideration of the position determined by the first subsystem. In particular, an identification procedure, which may be based on segmenting the interventional device in the second image, may be applied to a limited region of the second image only, wherein this limited region can be defined by using the position determined by the first subsystem. This can reduce the technical efforts required for carrying out the interventional procedure.

The interventional device is preferentially a needle or a catheter. In a preferred embodiment the interventional device is a brachytherapy catheter. The position determination device is preferentially adapted to determine the position of the interventional device by electromagnetic tracking or by using another tracking technique like optical shape sensing.

The first subsystem and the second subsystem are located at different places, i.e. at different sites, for instance, in different rooms of a same building or in different buildings. Preferentially, the stored position of the interventional device and the second image are registered to each other before being used by the planning and/or monitoring device for planning and/or monitoring purposes. In particular, the position determination device can be adapted to determine the position of the interventional device with respect to the first image generated by the first imaging device, i.e. the position determination device and the first imaging device can be registered to each other, wherein the first image and the second image can be registered to each other by the planning and/or monitoring device for registering the determined position of the interventional device to the second image via the first image.

The planning and/or monitoring device is a device for planning a treatment to be performed by using the interventional device and/or for monitoring a treatment performed by using the interventional device based on the stored position of the interventional device and the second image. Thus, the planning and/or monitoring device can be a) a device which is able to plan a treatment to be performed by using the interventional device based on the stored position of the interventional device and the second image, but which is not able to monitor a treatment performed by using the interventional device based on the stored position of the interventional device and the second image, b) a device being able to monitor a treatment performed by using the interventional device based on the stored position of the interventional device and the second image, but which is not able to plan a treatment to be performed by using the interventional device based on the stored position of the interventional device and the second image, or c) a device which is able to plan a treatment to be performed by using the interventional device based on the stored position of the interventional device and the second image and to monitor a treatment performed by using the interventional device based on the stored position of the interventional device and the second image.

In an embodiment the first subsystem further comprises a treatment plan providing unit for providing a treatment plan defining a planned position of the interventional device and a visualization generation unit for generating a visualization showing the first image, the determined position of the interventional device and the planned position while the interventional device is introduced into the subject. In particular, the treatment plan providing unit of the first subsystem can be adapted to provide a treatment plan defining the planned position of the interventional device and a treatment parameter defining an application of energy to the subject by using the interventional device for treating the subject, wherein the planning and/or monitoring device of the second subsystem can be adapted to update the treatment parameter of the provided treatment plan based on the stored position of the interventional device and the second image. For instance, the treatment can be a brachytherapy treatment and the treatment plan can define a planned position of a brachytherapy catheter within the subject and as treatment parameters dwell times and dwell positions of a radiation source within the brachytherapy catheter. The planning and/or monitoring device may be adapted to update the dwell times and/or the dwell positions based on the stored position of the brachytherapy catheter within the subject and the second image. This updating of the dwell times and/or the dwell positions can lead to an improved treatment plan and hence finally to an improved outcome of the treatment.

The interventional procedure can use one or several interventional devices, especially one or several brachytherapy catheters. Correspondingly, if several interventional devices are present, the treatment plan providing unit can be adapted to provide a treatment plan defining planned positions of the several interventional devices and treatment parameters defining an application of energy to the subject by using the interventional devices for treating the subject, wherein the planning and/or monitoring device can be adapted to update the treatment parameters of the provided treatment plan based on the stored positions of the interventional devices and the second image.

It is preferred that the first imaging device is an ultrasound or x-ray imaging device like an x-ray fluoroscopy device. An ultrasound imaging device or an x-ray imaging device allows for real-time imaging of the interventional device within the subject while introducing the interventional device and hence for a good image guidance during the introduction procedure with relatively low technical efforts.

It is further preferred that the second imaging device is a CT, MR, positron emission tomography (PET) or single photon emission computed tomography (SPECT) imaging device. These imaging devices may generate a second image showing certain features of the subject and/or of the interventional device better than the first image which might be an ultrasound image or an image generated by an x-ray imaging device like an x-ray fluoroscopy device. For instance, a target region, especially a tumor, may be better visible in a second image being an MR image than in a first image being an ultrasound image or an x-ray image generated by an x-ray fluoroscopy device. Using such a second image can therefore improve the guidance provided by the images and hence the outcome of the interventional procedure.

In an embodiment the planning and/or monitoring device is adapted to determine a target region within the subject in the second image and to plan the treatment, to be performed by using the interventional device based on the stored position of the interventional device and the determined target region. For instance, the system can be adapted to assist in performing a brachytherapy procedure, wherein the interventional device can be a brachytherapy catheter and wherein the planning and/or monitoring device can be adapted to plan the treatment to be performed by using the interventional device by determining a dwell position and a dwell time based on the stored position of the interventional device and the determined target region. This planning of the treatment can include an updating of an already generated treatment plan or an entirely new generation of a treatment plan. It can lead to an improved positioning of a radioactive radiation source within the subject for treating the target by using the dwell position and the dwell time and hence to an improved outcome of the treatment.

In an embodiment the system is adapted to assist in performing an interventional thermal therapy, wherein the interventional device is a heat providing needle and wherein the planning and/or monitoring device is adapted to monitor the interventional thermal therapy based on the stored position of the heat providing needle and the second image. For instance, the second imaging device can be an MR imaging device and the planning and/or monitoring device can be adapted to perform MR thermography based on the stored position of the heat providing needle and an MR image being the second image. Thus, MR thermography can be performed without necessarily requiring identifying the heat providing needle in the second image or by identifying the heat providing needle in the second image under consideration of the already determined position of the heat providing needle, thereby reducing the technical efforts required for performing the interventional procedure.

In another embodiment the system is adapted to assist in performing an interventional selective internal radiation therapy (SIRT), wherein the interventional device is a catheter for providing radioactive particles and wherein the planning and/or monitoring device is adapted to monitor a provision of the radioactive particles by the catheter based on the stored position of the catheter and the second image. Thus, for monitoring the provision of the radioactive particles by the catheter it is not necessarily required to identify the catheter in the second image for determining its position or the catheter can be identified in the second image in a simplified way under consideration of the already determined position of the catheter. This can reduce the technical efforts required for performing the interventional procedure.

In an embodiment the planning and/or monitoring device is adapted to plan the treatment, to be performed by using the interventional device, and/or to monitor a treatment performed by using the interventional device also based on the first image. Thus, the first image may not only be used for guiding the physician while introducing the interventional device into the subject, but also for planning the treatment and/or monitoring the treatment. The additional use of the first image can further improve the planning and/or monitoring and hence the outcome of the interventional procedure.

In a further aspect of the present invention a method for assisting in performing an interventional procedure is presented, wherein the method comprises:
generating a first image of a subject, while an interventional device is introduced into the subject, by a first imaging device of a first subsystem of a system as defined in claim 1,
determining the position of the interventional device within the subject relative to the first image by a position determination device of the first subsystem,
storing the determined position of the interventional device within the subject by a storage, after the interventional device has been introduced into the subject,
generating a second image of the subject by a second imaging device of a second subsystem of the system, wherein the first and second imaging devices are different imaging modalities, and
planning a treatment to be performed by using the interventional device and/or monitoring a treatment performed by using the interventional device based on the stored position of the interventional device and the second image by a planning and/or monitoring device of the second subsystem.

In a further aspect of the present invention a computer program for assisting in performing an interventional procedure is presented, wherein the computer program comprises program code means for causing a system as defined in claim 1 to carry out the method as defined in claim 12, when the computer program is run on the system.

It shall be understood that the system of claim 1, the method of claim 12 and the computer program of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
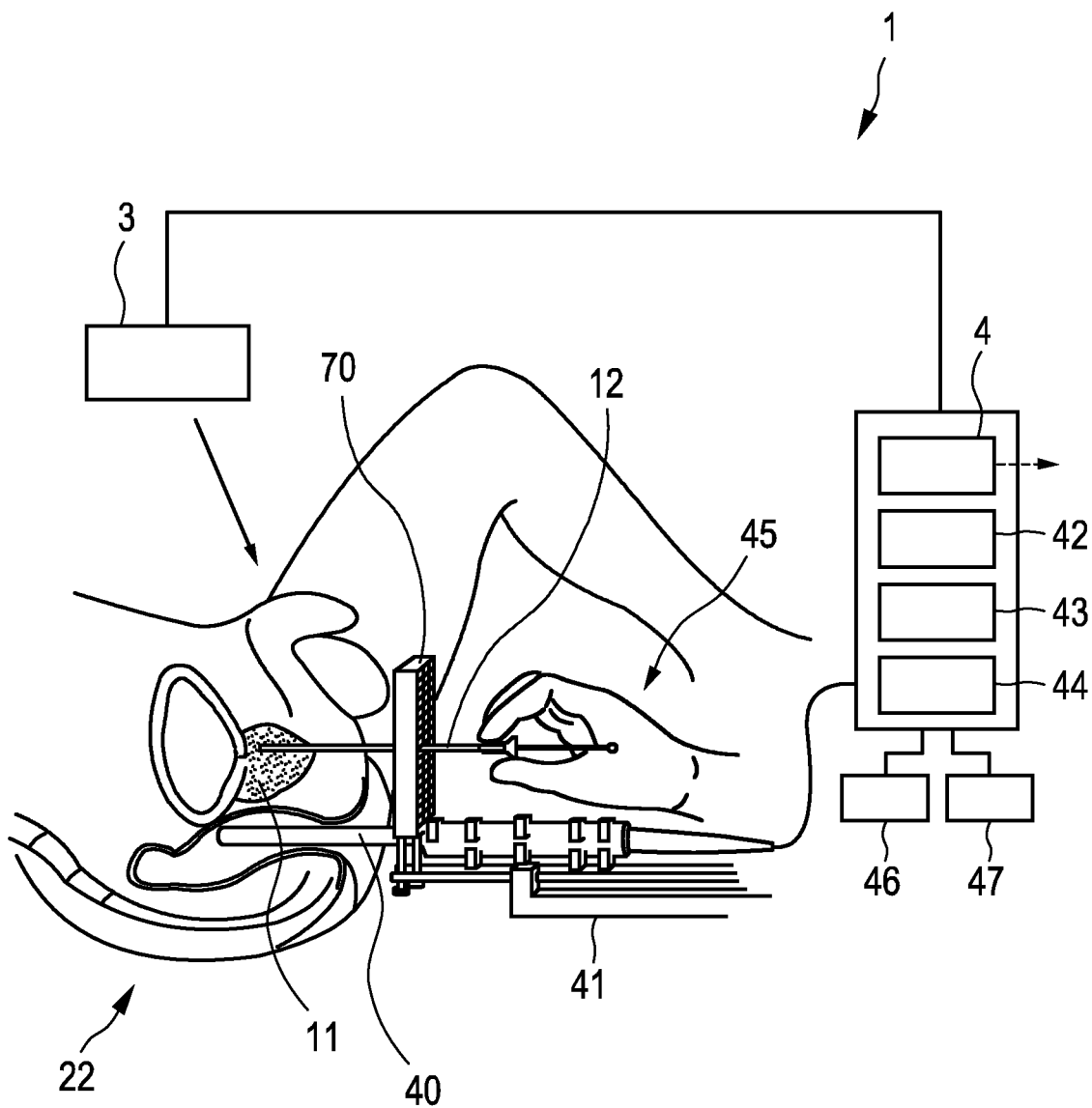
FIG. 1 shows schematically and exemplarily a first subsystem of an embodiment of a system for assisting in performing an interventional procedure.
Figure 2:
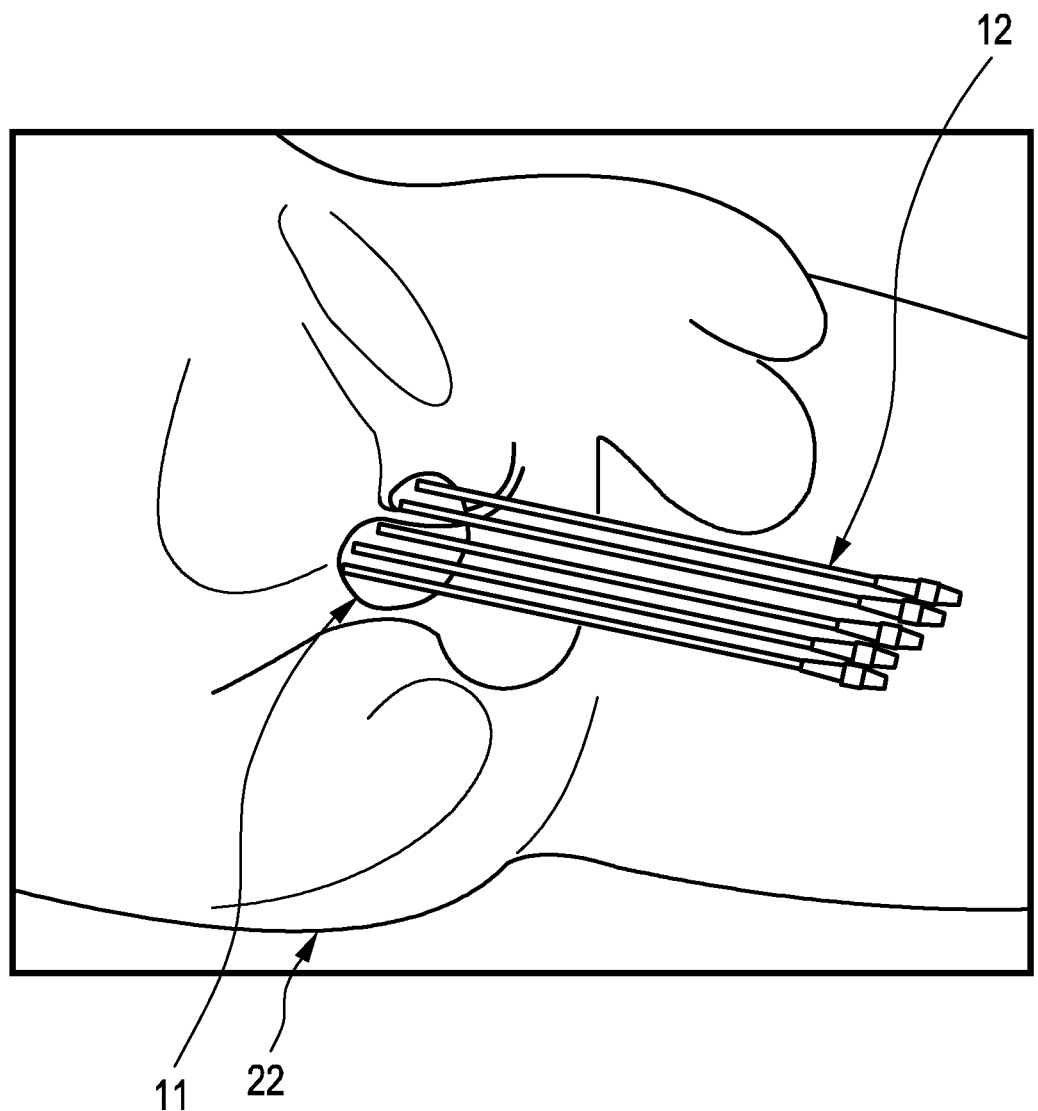
FIG. 2 shows schematically and exemplarily an arrangement of brachytherapy catheters within a prostate.
Figure 3:
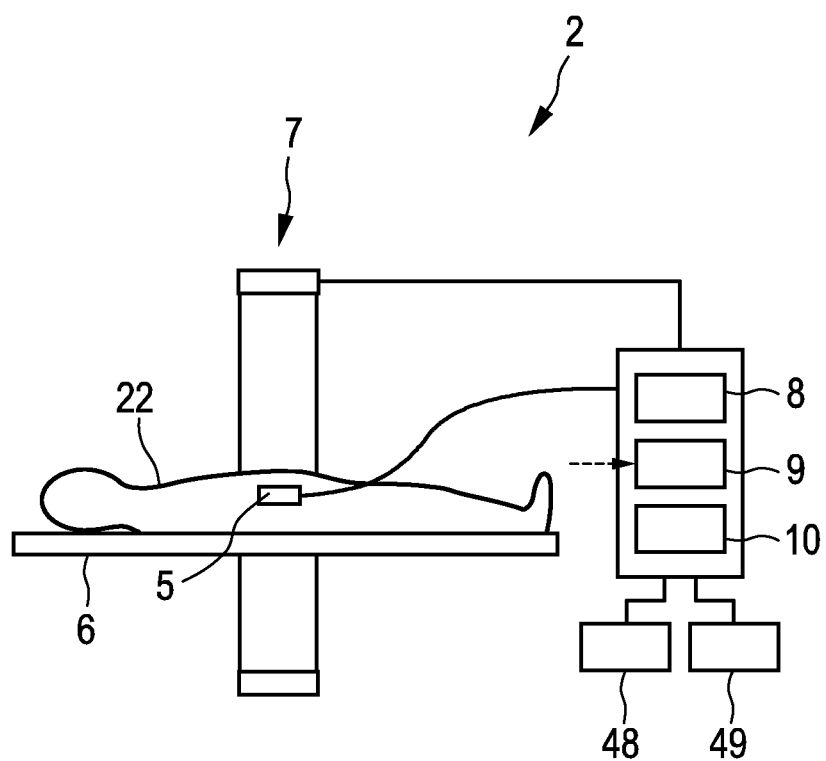
FIG. 3 shows schematically and exemplarily a second subsystem of the system for assisting in performing an interventional procedure.

FIGS. 1 and 3 schematically and exemplarily show subsystems of a system for assisting in performing an interventional procedure. In particular, FIG. 1 shows a first subsystem 1 comprising a first imaging device 40, 42 for generating a first image of a person 22 while an interventional device 12 is introduced into the person 22. In this embodiment the system is adapted to assist in performing an HDR brachytherapy procedure, wherein the interventional device 12 is a brachytherapy catheter to be introduced into the prostate 11 of the person 22 via a template 70. The template 70 is a holding element for holding and guiding the brachytherapy catheter 12 while introducing the brachytherapy catheter 12 into the prostate 11. The template 70 comprises a rectangular grid of openings through which the brachytherapy catheter 12 can be introduced into the prostate 11. Preferentially, several brachytherapy catheters 12 are introduced into the prostate 11 as schematically and exemplarily illustrated in FIG. 2.

The first imaging device comprises a transrectal ultrasound (TRUS) probe 40 and an ultrasound control unit 42 for controlling the TRUS probe 40 and for generating an ultrasound image based on signals received from the TRUS probe 40. The ultrasound image is a real-time image showing the person 22 while a physician introduces the brachytherapy catheter 12 into the prostate 11 by using his/her hand 45. The TRUS probe 40 is held by a holding element 41 which may be attached to a patient table, on which the person 22 may be arranged, or to another means having a fixed position with respect to the person 22.

The first subsystem 1 further comprises a position determination device 3 for determining the position of the respective brachytherapy catheter 12 within the person 22. In this embodiment the position determination device 3 is adapted to cooperate with an electromagnetic sensor included in the respective brachytherapy catheter 12 for determining the position of the respective brachytherapy catheter 12 by electromagnetic tracking. In another embodiment the position determination device can be adapted to determine the position of the respective brachytherapy catheter 12 in another way, for instance, by optical shape sensing. The first imaging device 40, 42 and the position determination device 3 are adapted such that the position of the respective brachytherapy catheter 12 within the person 22 is determined relative to the generated first image. The determined position of the respective brachytherapy catheter 12 within the person 22 is stored in a storage 4, after the respective brachytherapy catheter 12 has been introduced into the person 22. Thus, in the storage 4 at least the position of the respective brachytherapy catheter 12 is stored, which has been determined after the introduction and positioning procedure has been completed for the respective brachytherapy catheter 12 at the first subsystem 1.

The first subsystem 1 further comprises a treatment plan providing unit 43 for providing a treatment plan defining planned positions of the brachytherapy catheters 12 and, as further treatment parameters, dwell positions and dwell times for a radioactive radiation source within the brachytherapy catheters 12. The treatment plan providing unit 43 can be adapted to just provide an already determined treatment plan or the treatment plan providing unit 43 can be adapted to determine a treatment plan. For instance, the treatment plan providing unit 43 can be adapted to determine a treatment plan based on a given position, shape and dimension of a target region to be treated like a tumor within the prostate 11 by using known treatment plan algorithms which try to define the positions of the brachytherapy catheters and the dwell times and dwell positions of the radioactive radiation source within the brachytherapy catheters such that the target region receives as much as possible of the radiation provided by the radioactive radiation source and surrounding tissue receives no or only very little radiation. The position, shape and dimension of the target region can be obtained, for instance, by segmenting the target region in the first image or in another, pre-interventional image which might be, for instance, an MR image or a CT image.

The first subsystem 1 further comprises a visualization generation unit 44 for generating a visualization showing the first image, the determined position of the respective brachytherapy catheter 12, i.e. the tracked current position of the respective brachytherapy catheter 12, and the planned position of the respective brachytherapy catheter 12, which is defined by the treatment plan, while the respective brachytherapy catheter 12 is introduced into the person 22. The generated visualization is shown on a display 47 for providing an image guidance to the physician while the physician tries to introduce the respective brachytherapy catheter 12 in accordance with the provided treatment plan.

The first subsystem 1 further comprises an input unit 46 like a keyboard, a computer mouse, a touch pad et cetera, in order to allow the physician to provide inputs to the first subsystem 1. For instance, via the input unit 46 the physician can indicate that an image-guided introduction procedure including the generation of the visualization showing a real-time first image, a current tracked position of the respective brachytherapy catheter 12 and a respective planned position as defined by the provided treatment plan should be started or should be stopped. The input unit 46 can also be adapted to allow the physician to modify the position, shape and/or dimension of the target region and to indicate that a treatment plan should be determined based on the modified target region.

The first subsystem 1 is located at a first place within a hospital, i.e., for instance, in a first room of a hospital. The second subsystem schematically and exemplarily shown in FIG. 3 is located at a second place, i.e., for example, in a second room of the hospital. Thus, after the brachytherapy catheters 12 have been introduced into the person 22, the person 22 is moved to the second place, in order to continue the treatment procedure at the second place.

The second subsystem 2 comprises a second imaging device 7, 8 for generating a second image of the person 22 with the introduced brachytherapy catheters 12, wherein the first imaging device 40, 42 and the second imaging device 7, 8 are different imaging modalities. In this embodiment the second imaging device comprises an MR data acquisition unit 7 for acquiring MR data of the person 22 with the introduced brachytherapy catheters 12 and an MR control unit 8 for controlling the MR data acquisition unit 7 and for generating an MR image of the person 22 with the introduced brachytherapy catheters 12 based on the MR data acquired by the MR data acquisition unit 7. In other embodiments the second imaging device can also be another imaging modality like a CT imaging device or a nuclear imaging device like a PET imaging device or a SPECT imaging device.

The second subsystem further comprises a planning and/or monitoring device 9 for planning a treatment, to be performed by using the brachytherapy catheters 12, and/or for monitoring a treatment performed by using the brachytherapy catheters 12 based on the positions stored in the storage 4 of the first subsystem 1 and the generated second image. Thus, the planning and/or monitoring device 9 is adapted to receive the positions determined by the position determination device 3 of the first subsystem 1 and stored in the storage 4 and to use these stored positions of the brachytherapy catheters 12 for planning and/or monitoring purposes. The planning and/or monitoring device 9 is preferentially adapted to register the first image and the second image to each other such that, since the position of the brachytherapy catheters 12 have been determined relative to the first image, the positions of the brachytherapy catheters 12 are also known with respect to the second image. In this embodiment the planning and/or monitoring device 9 is adapted to identify the position, shape and dimension of the target region within the second image and to update the treatment plan provided by the treatment plan providing unit 43, especially the dwell times and dwell positions of the radioactive radiation source, based on the determined positions of the brachytherapy catheters 12 and the position, shape and dimension of the target region obtained from the second image. For instance, the planning and/or monitoring device 9 can be adapted to segment the target region in the second image and to provide a user interface, in order to allow the physician to modify the segmentation and, after the physician-based possible modification of the segmentation, confirm the position, shape and dimension of the target region. Also for this update of the already provided treatment plan known treatment planning algorithms can be used. The planning and/or monitoring device 9 can also be adapted to determine a new plan without using the treatment plan previously provided by the treatment plan providing unit 43 of the first subsystem 1. Also in this case the second image and the positions of the brachytherapy catheters 12 determined by the position determination device 3 and known treatment planning algorithms can be used.

The planning and/or monitoring device 9 can be adapted to provide a treatment plan which does not define dwell positions in all introduced brachytherapy catheters 12, if it is not necessary to move the radioactive radiation source 21 within each brachytherapy catheter 12 for treating the target region. Thus, the planning and/or monitoring device 9 can be adapted to ignore one or several brachytherapy catheters, if they are not needed for the treatment. Moreover, the planning and/or monitoring device 9 can be adapted to indicate if it is not able to generate a treatment plan sufficiently treating the target region based on the current positions and/or number of brachytherapy catheters. For instance, a dose distribution based on a treatment plan, which is as good as possible given the current positions and number of brachytherapy catheters, can be calculated by the planning and/or monitoring device 9 and shown on the display 47, especially overlaid with at least the segmented target region. The user can then decide whether the positions of one or several brachytherapy catheters should be changed and/or a further brachytherapy catheter should be added, wherein for this change of the positions and/or of the number of brachytherapy catheters the person may be moved back to the first subsystem 1 at the first place. The planning and/or monitoring device 9 may also be adapted to generate an optimized treatment plan by considering possible other positions of the brachytherapy catheters and/or a possible other number of brachytherapy catheters, wherein the resulting positions and the resulting number can be used at the first subsystem for introducing the brachytherapy catheters accordingly.

Figure 4:
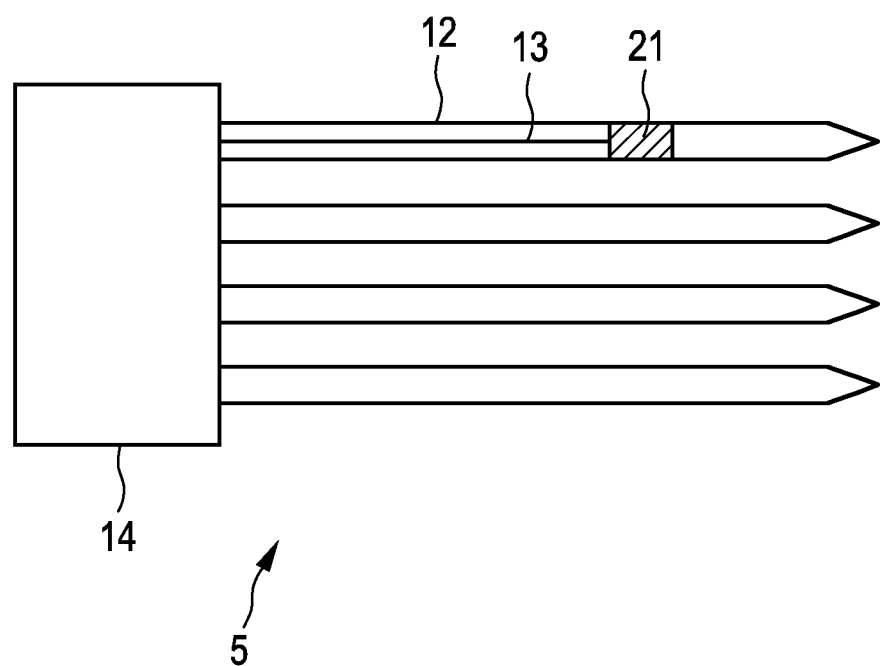
FIG. 4 shows schematically and exemplarily a placement device of the second subsystem.

The second subsystem 2 is adapted to actually perform the brachytherapy procedure by using a placing unit 5 for placing the radioactive radiation source within the brachytherapy catheters 12 in accordance with the treatment plan provided by the planning and/or monitoring device 9. The placing unit 5 is schematically and exemplarily illustrated in FIG. 4. The placing unit 5 comprises a drive wire 13 to which the radioactive radiation source 21 is attached, wherein the drive wire 13 with the radioactive radiation source 21 can be moved within each of the brachytherapy catheters 12 for placing the radioactive radiation source 21 at the planned dwell positions for the planned dwell times. The placing unit 5 further comprises a moving unit 14, which may also be regarded as being an afterloader and which is adapted to introduce the radioactive radiation source 21 into and to move the radioactive radiation source 21 within the different brachytherapy catheters 12 by using a motor. In particular, the moving unit 14 may be adapted to drive the radioactive radiation source 21 through an indexer that connects with the different brachytherapy catheters 12. For more details regarding this kind of placing the radioactive radiation source 21 within the person 22 reference is made to the publication "A Practical Guide to Quality Control of Brachytherapy Equipment" edited by J. Venselaar and J. Perez-Calatayud, European Society for Therapeutic Radiology and Oncology (2004), which is herewith incorporated by reference.

The placing unit can comprise further elements for assisting in placing the radioactive radiation source at the planned dwell positions for the planned dwell times within the person 22. For instance, the placing unit can comprise a template which can be used for holding the catheters at their positions within the person 22.

The placing unit 5, especially the moving unit 14, is controlled by a brachytherapy control unit 10 such that the radioactive radiation source 21 is placed at the planned dwell positions for the planned dwell times. The radioactive radiation source 21 is, for instance, Ir-192 or another radioactive radiation emitting source.

The planning and/or monitoring device 9 can also be adapted to monitor, for instance, a swelling of the prostate or of another part of the person 22 during the brachytherapy procedure by using the second image, which might be provided at different points in time, especially in real time, in order to monitor the swelling. The planning and/or monitoring device 9 can be further adapted to update the treatment plan based on the monitored swelling and to provide the updated treatment plan to the brachytherapy control unit 10, in order to allow for a real-time adaptation of the brachytherapy procedure in accordance with the swelling.

The second subsystem 2 further comprises an input unit 48 like a keyboard, a computer mouse or a touch pad and an output unit 49 like a display.

Figure 5:
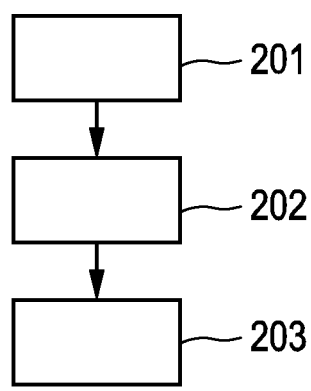
FIG. 5 shows a flowchart exemplarily illustrating an embodiment of a method for assisting in performing an interventional procedure.

In the following an embodiment of a method for assisting in performing an interventional procedure will exemplarily be described with reference to a flowchart shown in FIG. 5.

In step 201 the brachytherapy catheters 12 are introduced into the person 22 at a first place by using the first subsystem 1. During the insertion of the brachytherapy catheters 12 into the person 22 a real-time first image is generated by the first imaging device 40, 42 for guiding the physician. Moreover, in step 201 the positions of the brachytherapy catheters 12 within the person 22 are determined by the position determination device 3 of the first subsystem 1. At least the position of the respective brachytherapy catheter 12, after it has been introduced into the person 22, i.e. after the introduction procedure has been completed, is determined and this determined position is stored in the storage 4.

In step 202 the person 22 with the introduced brachytherapy catheters 12 is moved to the second place where the second subsystem 2 is located. In step 203 a second image of the person 22 is generated by the second imaging device 7, 8 of the second subsystem 2, and a treatment to be performed by using the brachytherapy catheters 12 is planned and/or a treatment performed by using the brachytherapy catheters 12 is monitored based on the positions of the brachytherapy catheters 12 stored in the storage 4 of the first subsystem 1 and the generated second image by the planning and/or monitoring device 9 of the second subsystem 2. In particular, a plan defining dwell positions and dwell times of the radioactive radiation source 21 within the brachytherapy catheters 12 is generated based on the stored positions of the brachytherapy catheters 12 and a position, shape and dimension of a target region obtained from the second image. Moreover, in step 203 at the second place the radioactive radiation source 21 can be moved within the brachytherapy catheters 12 in accordance with the generated treatment plan, in order to deliver a radiation dose to the target region, wherein during this delivery of the radiation dose a possible swelling of the prostate or of other parts of the person 22 can be monitored and wherein this monitored swelling can be used for updating the treatment plan. The updated treatment plan can be used by the brachytherapy control unit 10 for allowing for an adaptation of the current brachytherapy procedure to the swelling.

Figure 6:
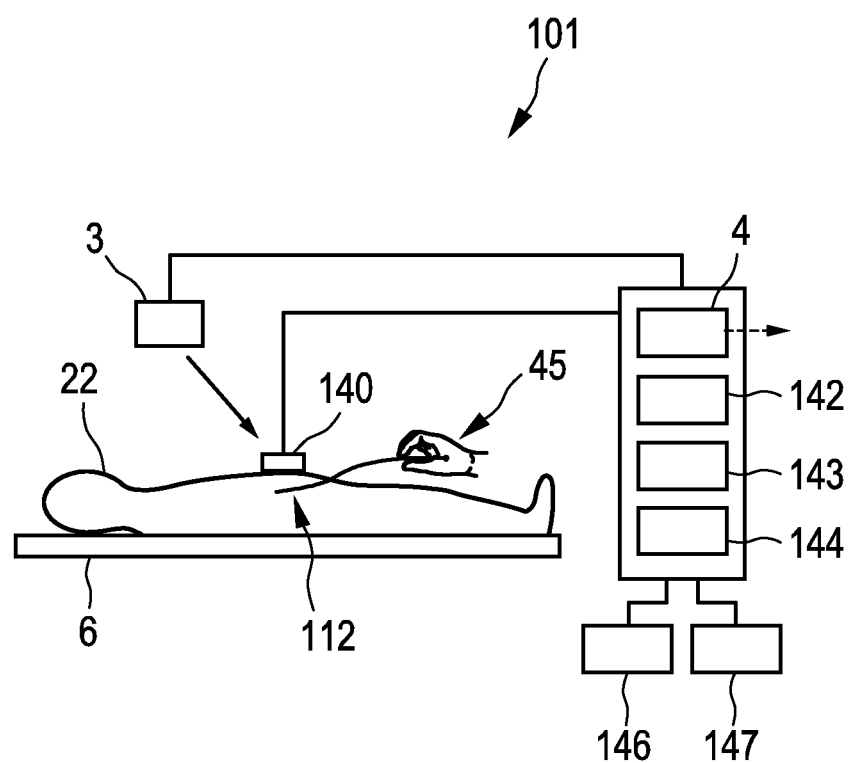
FIG. 6 shows schematically and exemplarily a first subsystem of another embodiment of the system for assisting in performing an interventional procedure.
Figure 7:
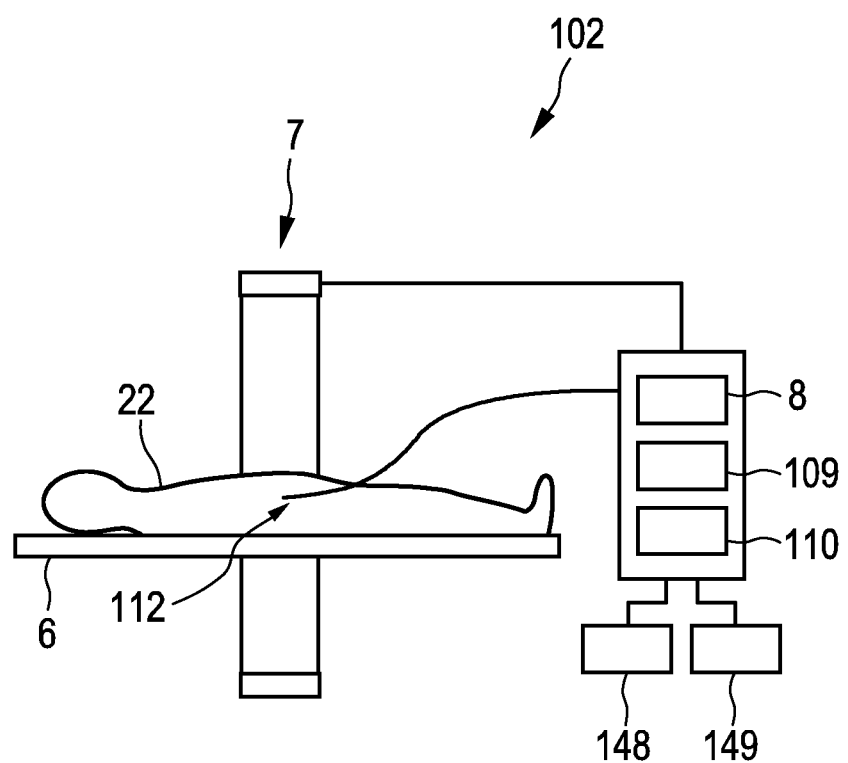
FIG. 7 shows schematically and exemplarily a second subsystem of the further embodiment of the system for assisting in performing an interventional procedure.

FIGS. 6 and 7 schematically exemplarily show first and second subsystems, respectively, of a further embodiment of a system for assisting in performing an interventional procedure. The first subsystem 101 is located at a first place and comprises a first imaging device for generating a first image of a person 22 while a heat providing needle 112 is introduced into the person 22 by using a hand 45 of a physician. The person 22 is arranged on a support means like a patient table 6. The first imaging device comprises an ultrasound probe 140 to be arranged on the outer skin of the person 22 and an ultrasound control unit 142 for generating a real-time ultrasound image as the first image. The first subsystem 101 further comprises a position determination device 3 for determining the position of the heat providing needle 112 within the person 22. Also in this embodiment the position determination device 3 and the heat providing needle 112 can be adapted to allow for a determination of the position of the heat providing needle 112 by electromagnetic tracking or optical shape sensing. The position of the heat providing needle 112 is preferentially determined in relation to the generated first image and stored in a storage 4. The first subsystem 101 further comprises a treatment plan providing unit 143 for providing a treatment plan defining at least a planned position of the heat providing needle 112. In this embodiment the treatment plan also defines, as further treatment parameters, an amount and/or direction of the heat to be applied. The treatment plan providing unit 143 can be adapted to provide an already determined treatment plan or to determine a treatment plan by itself. In the latter case the treatment plan providing unit 143 can be adapted to determine a treatment plan based on a position, shape and dimension of a target region to be treated by using known treatment planning algorithms. The position, shape and dimension of the target region can be determined by using the first image or by using a pre-interventional image which might an MR image or a CT image. A graphical user interface may be provided via a display 147 allowing the physician via an input unit 146 like a key board, a computer mouse, a touch pad, et cetera to modify the position, shape and dimension of the treatment region and to, after the position, shape and/or dimension has possibly been modified, confirm the position, shape and dimension of the target region.

The first subsystem 101 further comprises a visualization generation unit 144 for generating a visualization showing the first image, the determined position of the heat providing needle 112, i.e. the current position of the heat providing needle 112 as tracked by the position determination device 3, and the planned position of the heat providing needle 112, while the heat providing needle 112 is introduced into the person 22. This visualization is preferentially generated in real time and shown on the display 147, in order to provide real-time image guidance to the physician.

The second subsystem 102 is located at a second place and comprises a second imaging device 7, 8 for generating a second image of the person 22 with the introduced heat providing needle 112. Also in this embodiment the second imaging device comprises an MR data acquisition unit 7 and an MR control unit 8 for generating an MR image as the second image. The second subsystem 102 further comprises a planning and/or monitoring device 109 for planning a treatment to be performed by using the heat providing needle 112 and/or for monitoring a treatment performed by using the heat providing needle 112 based on the stored position of the heat providing needle 112 and the second image. In particular, the planning and/or monitoring device 109 is adapted to monitor an interventional thermal therapy based on the stored position of the heat providing needle 112 and the second image, wherein in this case the second image is preferentially a real-time image. For instance, the planning and/or monitoring device 109 can be adapted to perform MR thermography based on the stored position of the heat providing needle 112 and the MR image, wherein the resulting temperature distribution can be shown on a display 149. In addition, the determined temperature distribution can be used by a thermal therapy control unit 110 for controlling the application of heat to the target region depending on the determined temperature distribution. The planning and/or monitoring device 109 can also be adapted to update a treatment plan provided by the treatment plan providing unit 143 depending on a position, shape and dimension of a target region obtained from the second image and depending on the stored position of the heat providing needle 112. This update of the treatment plan can include a modification of the amount and/or direction of heat to be applied to the target region. The planning and/or monitoring device 109 can also be adapted to generate a new treatment plan based on the stored position of the heat providing needle 112 and a position, shape and dimension of the target region obtained from the second image without using the treatment plan provided by the treatment plan providing unit 143. Also the second subsystem 102 comprises an input unit 148 like a keyboard, a computer mouse, a touch pad, et cetera.

In a further embodiment the system can be adapted to assist in performing a SIRT procedure, wherein the interventional device can be a catheter for providing radioactive particles, wherein the catheter may be placed by using, for instance, a first subsystem located at a first place as described above with reference to FIG. 6, wherein a first imaging device generates a first image of a person while a catheter is introduced into the person, a position determination device like an electromagnetic tracking device determines the position of the catheter within the person and a storage stores the determined position of the catheter within the person, after the catheter has been introduced into the person. Moreover, a second subsystem located at a second place as described, for instance, with respect to FIG. 7 may be used for monitoring a provision of the radioactive articles by the catheter based on the stored position of the catheter and a second image. Thus, a second imaging device may generate a second image of the person with the introduced catheter, wherein the first and second imaging devices are different imaging modalities, and a planning and/or monitoring device may monitor the provision of the radioactive particles by the catheter based on the stored position of the catheter and the second image. The provision of the radioactive particles can be controlled by a SIRT control unit in accordance with a corresponding treatment plan, wherein this treatment plan may be updated based on the monitored provision of the radioactive particles by the treatment and/or monitoring device. The updated treatment plan may be used by the SIRT control unit for adapting the SIRT to the current provision of the radioactive particles, especially to the current distribution of the radioactive particles within the person. The planning and/or monitoring device may also be adapted to generate a new treatment plan based on the determined position of the catheter and based on the second image, wherein the SIRT control unit can control the provision of the radioactive particles based on the new treatment plan. Also in this embodiment the first image is preferentially an ultrasound image and the second image is preferentially an MR image, wherein the first subsystem and the second subsystem are preferentially located in different rooms of a hospital.

The described systems preferentially relate to the field of interventional oncology, in particular to multi-modality image guided focal therapy. At the first place by using the first subsystem an interventional device like a needle or another instrument is positioned inside or close to, for instance, a tumor to deliver a therapeutic dose of an ablative energy, wherein the focal therapy may refer to brachytherapy, cryotherapy, radio frequency (RF) ablation, microwave ablation, laser ablation, electroporation, et cetera. The first subsystem supports this positioning by providing the first image, which is preferentially a real-time image, and by integrating a navigation technology into the interventional device like electromagnetic tracking or optical shape sensing tracking, in order to allow for a display of the position of the interventional device in combination with the first image which might be a medical image of a lesion.

The system with the first subsystem comprising the first imaging device and the second subsystem having the second imaging device can allow for a generation of images of different imaging modalities during the intervention. In particular, the integral system supports multi-modal image guidance at different locations within a hospital. A treatment can be started on one subsystem using one imaging modality, after which the treatment can be continued on another subsystem combining initial results obtained by using the first subsystem with one or several second images that support a next task to be carried out by using the second subsystem.

In an embodiment the second imaging device of the second subsystem is a computed tomography imaging device for generating a computed tomography image as the second image. In this embodiment the planning and/or monitoring device is adapted to identify the interventional device in the computed tomography image, in order to determine its position, and to generate a treatment plan for treating the person based on this determined position. The identification of the interventional device in the computed tomography image uses the position determined by the position determination device of the first subsystem, for instance, for defining a region in the computed tomography image, to which a segmentation algorithm for identifying the interventional device should be applied. For example, the position determination device can determine the position of a brachytherapy catheter at a first place, wherein the brachytherapy catheter has been introduced into the person under ultrasound guidance, i.e. while the first imaging device has generated a real-time ultrasound image. The tracked position of the brachytherapy catheter can be provided to the planning and/or monitoring device of the second subsystem, in order to generate a brachytherapy treatment plan based on this position and the computed tomography image being the second image in this embodiment, wherein in the computed tomography image the current position of the brachytherapy catheter can be determined by using, inter alia, the electromagnetically tracked position of the brachytherapy catheter determined by the position determination device of the first subsystem.

Although in above described embodiments the first imaging device is an ultrasound imaging device, in other embodiments the first imaging device can also be another imaging modality. For instance, the first imaging device can be an interventional x-ray imaging device like an x-ray fluoroscopy device. In particular, in case of SIRT an interventional x-ray imaging device can be used for providing image guidance while navigating the catheters towards the target location. Once the catheter is in place, the person is moved to another location, for instance, to another room, with a second subsystem comprising a second imaging device like an MR imaging device or a PET/CT imaging device, wherein the images generated by the respective imaging device can be used for providing a controlled release of the radioactive particles, including adaptive therapy modulation. For instance, the planning and/or monitoring device can be adapted to determine the distribution of radioactive particles within the person based on the second image, to adapt a treatment plan based on the determined distribution of radioactive particles and to provide the adapted treatment plan to a control unit controlling the release of the radioactive particles.

Preferentially, the first image, the position of the interventional device determined by the position determination device and the second imaging device are registered to each other. In an embodiment the planning and/or monitoring device can be adapted to register the first image and the second image with respect to each other based on organ delineations in the first and second images, wherein these delineations in the first and second images may be determined automatically by using known segmentation algorithms, manually or semi-automatically, wherein in the latter case a user is allowed to modify an automatically generated segmentation. However, the planning and/or monitoring device may of course also be adapted to use other registration techniques which may just be based on the image intensities.

Although in above described embodiments certain systems for assisting in performing certain interventional procedures have been described, in other embodiments also other systems for assisting in performing other interventional procedures can be used, which comprise a first subsystem and a second subsystem as defined in claim 1. For instance, the system can be adapted to assist in performing a cryotherapy procedure, a pulsed dose rate (PDR)

brachytherapy procedure, a low dose rate (LDR) brachytherapy procedure, a laser ablation procedure, et cetera.

Although in above described embodiments the system comprises a first subsystem and a second subsystem, the system can also comprise more than two subsystems, wherein a position of an interventional device determined in a first subsystem can be stored and used by another subsystem together with an image generated by the other subsystem for treatment planning and/or monitoring purposes.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Procedures like a provision of a treatment plan or a generation of a visualization performed by several units of the first subsystem or like the planning and/or monitoring of a treatment performed by a unit of the second subsystem can be performed by any other number of units or devices of the respective subsystem. These procedures and/or a control of the system for assisting in performing an interventional procedure in accordance with the method for assisting in performing an interventional procedure can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for assisting in performing an interventional procedure. The system comprises a first subsystem and a second subsystem at different places, especially in different rooms. At a first place the first subsystem a) generates a first image of a subject while an interventional device is introduced into the subject and b) determines the position of the interventional device within the subject. At a second place the second subsystem a) generates a second image of the subject with the introduced interventional device and b) plans and/or monitors a treatment based on the second image and the already determined position of the interventional device, i.e. the second subsystem does not need to start a completely new position determination procedure, thereby reducing technical efforts. Moreover, the first and second images are generated by different imaging modalities which allows for, for instance, improved image guidance, planning and/or monitoring.

The invention claimed is:

1. A system for assisting in performing an interventional procedure in which an associated interventional device is introduced into a subject, the system comprising:
a first subsystem that receives a first image of the subject generated by an associated first imaging device while the associated interventional device is introduced into the subject, the first subsystem comprising:
a position determination device for determining the position of the associated interventional device within the subject relative to the first image, and
a storage for storing the determined position of the associated interventional device within the subject, after the associated interventional device has been introduced into the subject,
a second subsystem that receives a second image of the subject generated by an associated second imaging device with the introduced associated interventional device, wherein the associated first imaging device and the associated second imaging device are different imaging modalities, the second subsystem comprising:
a planning and monitoring device for: (i) planning a treatment to be performed by using the associated interventional device and (ii) receiving the stored position of the associated interventional device from the storage of the first subsystem, and (iii) monitoring the treatment performed by using the associated interventional device based on the received position of the associated interventional device and the second image,
wherein the first subsystem and the second subsystem are located at different places.

2. The system as defined in claim 1, wherein the first subsystem further comprises:
a treatment plan providing unit for providing a treatment plan defining a planned position of the associated interventional device,
a visualization generation unit for generating a visualization showing the first image, the determined position of the associated interventional device and the planned position while the associated interventional device is introduced into the subject.

3. The system as defined in claim 2, wherein the treatment plan providing unit is adapted to provide a treatment plan defining the planned position of the associated interventional device and a treatment parameter defining an application of energy to the subject by using the associated interventional device for treating the subject, wherein the planning and monitoring device is adapted to update the treatment parameter of the provided treatment plan based on the stored position of the associated interventional device and the second image.

4. The system as defined in claim 2, wherein the system is adapted to assist in performing an interventional brachytherapy procedure, wherein the associated interventional device is an associated brachytherapy catheter, wherein the treatment plan providing unit is adapted to provide the treatment plan such that it defines a planned position of the associated brachytherapy catheter, a dwell position within the associated brachytherapy catheter and a dwell time for a radiation source.

5. The system as defined in claim 1, wherein the associated first imaging device is an ultrasound or x-ray imaging device.

6. The system as defined in claim 1, wherein the associated second imaging device is a computed tomography, magnetic resonance, positron emission tomography or single photon emission computed tomography imaging device.

7. The system as defined in claim 1, wherein the planning and monitoring device is adapted to determine a target region within the subject in the second image and to plan the treatment, to be performed by using the associated interventional device, based on the stored position of the associated interventional device and the determined target region.

8. The system as defined in claim 7, wherein the system is adapted to assist in performing an interventional brachytherapy procedure, wherein the associated interventional device is a brachytherapy catheter, wherein the planning and monitoring device is adapted to plan the treatment to be performed by using the associated interventional device by determining a dwell position and a dwell time based on the stored position of the associated interventional device and the determined target region.

9. The system as defined in claim 1, wherein the system is adapted to assist in performing an interventional thermal therapy, wherein the associated interventional device is an associated heat providing needle, wherein the planning and monitoring device is adapted to monitor the associated interventional thermal therapy based on the stored position of the associated heat providing needle and the second image.

10. The system as defined in claim 1, wherein the system is adapted to assist in performing an interventional selective internal radiation therapy, wherein the associated interventional device is an associated catheter for providing radioactive particles, wherein the planning and monitoring device is adapted to monitor a provision of the radioactive particles by the associated catheter based on the stored position of the associated catheter and the second image.

11. A method for assisting in performing an interventional procedure, the method comprising:
   generating a first image of a subject, while the interventional device is introduced into the subject, by the first imaging device of the first subsystem of the system as defined in claim 1,
   determining the position of the interventional device within the subject relative to the first image by the position determination device of the first subsystem at a first location,
   storing the determined position of the interventional device within the subject by the storage, after the interventional device has been introduced into the subject,
   transferring the stored position of the interventional device to the second subsystem of the system at a second place;
   generating a second image of the subject by the second imaging device of the second subsystem, wherein the first and second imaging devices are different imaging modalities and wherein the second place is different from the first place, and
   at least one of planning a treatment to be performed by using the interventional device and monitoring a treatment performed by using the interventional device based on the received position of the interventional device and the second image by at least one of a planning and monitoring device of the second subsystem.

12. A non-transitory computer-readable medium carrying a computer program for assisting in performing an interventional procedure, the computer program comprising program code means for causing a computer processor to perform the method of claim 11.

13. A system for assisting in performing an interventional procedure, the system comprising:
   a computer storage configured to store a determined position of an interventional device within a subject, after the interventional device has been introduced into the subject,
   wherein the position of the interventional device within the subject was determined relative to a first diagnostic image using a tracker,
   wherein the first diagnostic image was generated by a first diagnostic imaging system while the interventional device was introduced into the subject;
   a second diagnostic imaging system configured to receive the determined position of the interventional device from the computer storage and generate a second diagnostic image of the subject with the interventional device introduced in the subject, wherein the first and second diagnostic imaging systems are different imaging modalities; and
   a computer processor that is configured to execute instructions to plan the treatment to be performed using the interventional device and to monitor the treatment performed using the interventional device based on the received position of the interventional device and the second diagnostic image, wherein the first diagnostic imaging system and the second diagnostic imaging system are located in different rooms.

14. The system of claim 13, wherein the computer processor is configured to execute further instructions to generate a visualization showing the first diagnostic image, the determined position of the associated interventional device and the planned position while the associated interventional device is introduced into the subject.

15. The system as defined in claim 13, wherein the system is adapted to assist in performing an interventional thermal therapy, wherein the interventional device is an ablation providing needle, wherein the planning and monitoring device is adapted to monitor an interventional ablation therapy based on the stored determined position of an associated heat providing needle and the second diagnostic image.

16. A method for assisting in performing an interventional procedure, the method comprising:
   generating a first image of a subject while an interventional device is being introduced into the subject using a first imaging modality;
   determining a position of the interventional device within the subject relative to the first image, after the interventional device has been introduced into the subject, using a tracker;
   storing the determined position of the interventional device within the subject relative to the first image, after the interventional device has been introduced into the subject, in a computer memory;
   receiving the stored determined position of the interventional device from the computer memory and generating a second diagnostic image of the subject with the interventional device introduced in the subject using a second imaging modality, wherein the first and second imaging modalities are different imaging modalities; and
   monitoring a treatment performed by using the interventional device based on the received stored determined position of the interventional device and the second image.

17. A non-transitory computer-readable medium carrying software configured to control one or more computer processors to perform the method as defined in claim 16.

18. A system for assisting in performing an interventional procedure, the system comprising:
   an interventional device; and
   one or more computer processors configured to perform the method defined in claim 16.

19. The method of claim 16, wherein the first imaging modality and the second imaging modality are located in different rooms.

\* \* \* \* \*